United States Patent [19]

Timmler et al.

[11] Patent Number: 4,776,877
[45] Date of Patent: Oct. 11, 1988

[54] TRIAZOLYL-ALKANONES OR TRIAZOLYL-ALKANOLS

[75] Inventors: Helmut Timmler; Wolfgang Krämer; Karl H. Büchel, all of Wuppertal; Helmut Kaspers, Leverkusen; Wilhelm Brandes, Cologne, all of Fed. Rep. of Germany

[73] Assignee: Bayer Aktiengesellschaft, Leverkusen, Fed. Rep. of Germany

[21] Appl. No.: 291,700

[22] Filed: Aug. 10, 1981

Related U.S. Application Data

[60] Division of Ser. No. 792,756, May 2, 1977, which is a continuation of Ser. No. 586,121, Jun. 11, 1975, abandoned.

[30] Foreign Application Priority Data

Jun. 29, 1974 [DE] Fed. Rep. of Germany ....... 2431407

[51] Int. Cl.$^4$ ................ C07D 249/08; A01N 43/653; A61K 31/41
[52] U.S. Cl. ........................................ 71/92; 514/383; 548/262
[58] Field of Search ........................ 548/262; 424/269; 71/92

[56] References Cited

U.S. PATENT DOCUMENTS 4,079,143 3/1978 Balasubramanyan et al. ..... 424/269

FOREIGN PATENT DOCUMENTS 1000917 8/1965 United Kingdom ................ 548/262

Primary Examiner—Richard L. Raymond
Assistant Examiner—D. L. Dinner
Attorney, Agent, or Firm—Sprung Horn Kramer & Woods

[57] ABSTRACT

Triazolyl-alkanones or triazolyl-alkanols of the formula

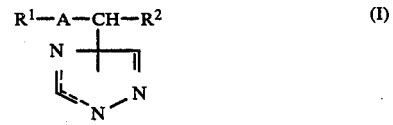

in which
$R^1$ is alkyl, cycloalkyl, aryl or substituted aryl, and
$R^2$ is hydrogen, alkyl, cycloalkyl, aryl or substituted aryl, or
$R^1$ and $R^2$ are joined to form an aliphatic ring, and
A is a keto group or a CH(OH) group,
or a salt thereof which possess fungicidal, microbicidal and plant-growth regulating properties.

8 Claims, No Drawings

TRIAZOLYL-ALKANONES OR TRIAZOLYL-ALKANOLS

This is a division of application Ser. No. 792,756, filed May 2, 1977, now pending, which is a continuation of application Ser. No. 586,121, filed June 11, 1975, now abandoned.

The present invention relates to and has for its objects the provision of particular new triazolyl-alkanones or triazolyl-alkanols or salts thereof which possess fungicidal, microbicidal and plant growth-regulating properties, active compositions in the form of mixtures of such compounds with solid and liquid dispersible carrier vehicles, and methods for producing such compounds and for using such compounds in a new way especially for combating or controlling fungi, microbes and plant growth, with other and further objects becoming apparent from a study of the within specification and accompanying examples.

It has already been disclosed in U.S. Pat. No. 3,321,366 and German Published Specification DOS No. 1,795,249 that trityl-imidazoles and trityl-1,2,4-triazoles, such as triphenylimidazole and triphenyl-1,2,4-triazole (Compound A), possess fungicidal activity. However, their action is not always entirely satisfactory, especially if low amounts and low concentrations are used.

The present invention provides compounds which are triazolyl-alkanones or triazolyl-alkanols of the general formula

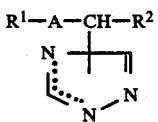

(I)

The compounds according to the invention are derivatives of 1,2,4-triazole, in which the azole radical may be linked in the 1-position or in the 4-position.

Preferably, $R^1$ is straight-chain or branched alkyl with up to 6, especially with up to 4, carbon atoms, of which methyl, ethyl, isopropyl and tertiary butyl may be mentioned as examples, or $R^1$ is cycloalkyl with 3 to 8, especially 5 or 6, carbon atoms, of which cyclohexyl may be mentioned as an example, or $R^1$ is phenyl, which can carry any of the following substituents: alkyl or alkoxy each with up to 4, especially with up to 2, carbon atoms, of which methyl and methoxy may be mentioned as examples; haloalkyl with up to 4 carbon atoms and up to 5 halogen atoms, especially with up to 2 carbon atoms and up to 3 identical or different halogen atoms, preferred halogens being fluorine and chlorine, of which trifluoromethyl may be mentioned as an example; halogen, especially fluorine or chlorine; cyano; nitro; dialkylamino with up to 4, especially with up to 2, carbon atoms in each alkyl moiety; alkoxycarbonyl with 2 to 4, especially 2 or 3, carbon atoms, of which methoxycarbonyl and ethoxycarbonyl may be mentioned as examples; alkylsulfonyl or haloalkylsulfonyl each with up to 4, especially with up to 2, carbon atoms, and, in the latter case, with up to 5, especially with up to 3, identical or different halogen atoms, preferred halogens being fluorine and chlorine, of which methylsulfonyl and trifluoromethylsulfonyl may be mentioned as examples; phenoxy, phenylthio or phenylsulfonyl; phenyl, chlorophenyl, benzyl, chlorobenzyl or phenylethyl as substituents on the said phenyl; and $R^2$ is hydrogen or any of the groups mentioned for $R^1$; or $R^1$ and $R^2$ together form a —$(CH_2)_3$— or —$(CH_2)_2$— group.

Surprisingly, the active compounds according to the invention exhibit a substantially greater fungicidal action than the known compounds triphenylimidazole and triphenyl-1,2,4-triazole. The active compounds according to the invention thus represent an enrichment of the art.

The invention also provides a process for the preparation of a compound of the invention in which, when A is a keto group, (a) a haloketone of the general formula

(II)

in which
$R^1$ and $R^2$ have the abovementioned meanings and
Hal is chlorine or bromine
is reacted with 1,2,4-triazole in the presence of an acid-binding agent and optionally in the presence of a diluent, or (b) a hydroxyketone of the general formula

(III)

in which
$R^1$ and $R^2$ have the above mentioned meanings
is reacted with thionyl-bis-1,2,4-triazole-(1) of the formula

(IV)

optionally in the presence of a diluent, or, when A is a CH(OH) group, (c) a compound obtained by process variant (a) or (b) is reduced either 1. with hydrogen in the presence of a catalyst and optionally in the presence of a polar solvent, or
2. with aluminum isopropylate in the presence of a solvent, or
3. with a complex hydride optionally in the presence of a polar solvent, or
4. with formamidine-sulfinic acid and alkali metal hydroxide optionally in the presence of a polar solvent.

If (ω-bromo)-(ω-phenyl)-acetophenone and 1,2,4-triazole are used as starting materials according to process variant (a), the course of the reaction can be represented by the following formula scheme:

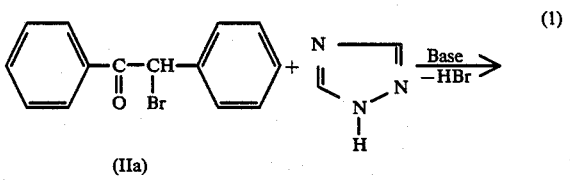

(1)

(IIa)

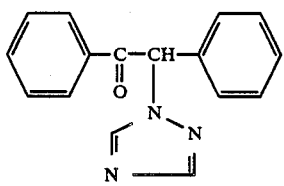

If bis-tert.-butyl-acyloin, thionyl chloride and 1,2,4-triazole are used as starting materials according to process variant (b), the course of the reaction can be represented by the following formula scheme:

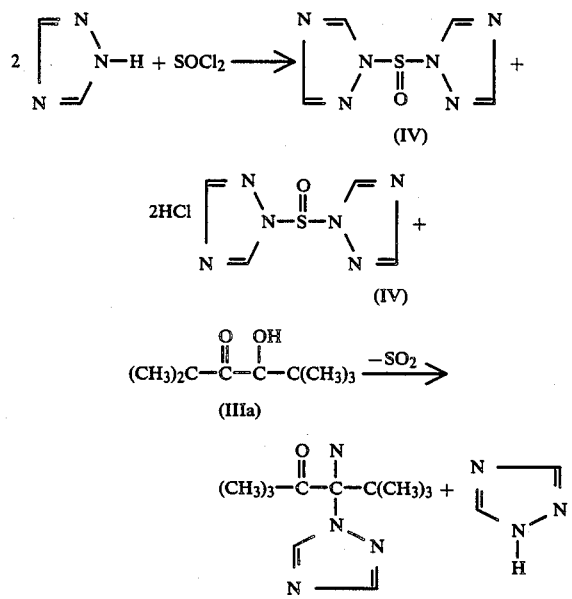

The reduction reactions according to process variant (c) may be illustrated by an example:

If ω-[1,2,4-triazolyl-(1)]-2,4-dichloro-acetophenone and hydrogen are used as starting materials, the course of the reaction according to process sub-variant (c/1) can be represented by the following formula scheme:

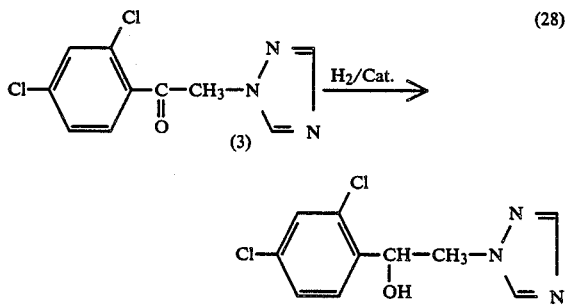

The reduction reactions according to process sub-variants (c/2) to (c/4) are similar in type and can be formulated analogously.

The following may be mentioned as haloketones of formula (II) to be used as starting materials for process variant (a):

1-bromo-1-phenyl-3,3-dimethyl-butan-2-one, 1-bromo-1-(4'-chlorophenyl)-3,3-dimethyl-butan-2-one, 1-bromo-1-(3'-chlorophenyl)-3,3-dimethyl-butan-2-one, 1-bromo-1-(2',4'-dichlorophenyl)-3,3-dimethyl-butan-2-one, 1-bromo-1-(2',6'-dichlorophenyl)-3,3-dimethyl-butan-2-one, 1-bromo-1-(2',5'-dichlorophenyl)-3,3-dimethyl-butan-2-one, 1-bromo-1-(4'-methoxyphenyl)-3,3-dimethyl-butan-2-one, 1-bromo-1-phenyl-propan-2-one, 1-bromo-1-(2'-methylphenyl)-propan-2-one, 1-bromo-1-(2'-methyl-4'-chlorophenyl)-propan-2-one, 1-bromo-1-(4'-trifluoromethylphenyl)-propan-2-one, 1-bromo-1-(4'-nitrophenyl)-propan-2-one, ω-bromo-ω-methyl-acetophenone, ω-bromo-ω-phenyl-acetophenone, ω-bromo-acetophenone, ω-bromo-ω-(4'-chlorophenyl)-acetophenone, ω-chloro-ω-(3'-chlorophenyl)-acetophenone, ω-bromo-ω-(2',4'-dichlorophenyl)-acetophenone, ω-bromo-ω-(4'-methylphenyl)-acetophenone, ω-chloro-ω-(2'-chloro-4'-methyl-phenyl)-acetophenone, ω-chloro-ω-(2'-methyl-4'-chlorophenyl)-acetophenone, ω-bromo-ω-(2'-methylphenyl)-acetophenone, ω-chloro-ω-(2',4'-dichlorophenyl)-4-chloroacetophenone, ω-chloro-ω-methyl-2,4-dichloroacetophenone, ω-bromo-ω-(4'-chlorophenyl)-4-fluoroacetophenone, ω-bromo-3-chloro-acetophenone, ω-bromo-3-trifluoromethylacetophenone, ω-chloro-3,4-dichloroacetophenone and ω-chloro-4-methoxyacetophenone.

Haloketones of the formula (II) are disclosed in Bulletin de la Société Chimique de France 1955, pages 1,363–1,383 and can be prepared in accordance with the processes described in that publication as well as in the examples hereinbelow.

The following may be mentioned as examples of hydroxyketones of formula (III) required as starting materials for process variant (b): 1-hydroxy-1-phenyl-3,3-dimethyl-butan-2-one, 1-hydroxy-1-(4'-chlorophenyl)-3,3-dimethyl-butan-2-one, 1-hydroxy-1-(2',4'-dichlorophenyl)-3,3-dimethyl-butan-2-one, 1-hydroxy-1-(4'-methoxyphenyl)-3,3-dimethyl-butan-2-one, 1-hydroxy-1-(2'-methylphenyl)-3,3-dimethyl-butan-2-one, 1-hydroxy-1-(4'-bromophenyl)-propan-2-one, 1-hydroxy-1-(2',4',6'-trichlorophenyl)-propan-2-one, 1-hydroxy-1-(4'-tert.-butyl-phenyl)-propan-2-one, 1-hydroxy-1-(4'-isopropyl-phenyl)-propan-2-one, 1-hydroxy-1-(2'-nitrophenyl)-propan-2-one, 1-hydroxy-1-(p-diphenyl)-propan-2-one, ω-hydroxy-ω-methyl-acetophenone, ω-hydroxy-acetophenone, ω-hydroxy-ω-phenyl-acetophenone, ω-hydroxy-ω-(4'-chlorophenyl)-acetophenone, ω-hydroxy-ω-(2'-chlorophenyl)-acetophenone, ω-hydroxy-ω-(2'-methylphenyl)-acetophenone, ω-hydroxy-ω-(2'-chloro-4'-methylphenyl)-acetophenone, ω-hydroxy-4-chloroacetophenone, ω-hydroxy-3-methylacetophenone and ω-hydroxy-2,4-dichloroacetophenone.

Hydroxyketones of the formula (III) are disclosed in Organic Reactions 4(1948) 256–268 and Bulletin de la Societe Chimique de France 1950, pages D83–D92 and can be prepared according to J. Org. Chem. (1959) 385–387 and the examples hereinbelow.

It is often preferable that salts of the compounds of the formula (I) should be salts of physiologically tolerated acids. Preferred ones include the hydrogen halide acids, for example hydrochloric acid and hydrobromic acid (especially hydrochloric acid), phosphoric acid, nitric acid, monofunctional and bifunctional carboxylic acids and hydroxycarboxylic acids, for example acetic acid, maleic acid, succinic acid, fumaric acid, tartaric acid, citric acid, salicyclic acid, sorbic acid and lactic acid, and 1,5-naphthalene-disulufonic acid.

Possible diluents for the reaction of process variant (a) include inert organic solvents. Preferred ones include ketones, such as diethyl ketone, and especially acetone and methyl ethyl ketone; nitriles, such as propionitrile, and especially acetonitrile; alcohols, such as ethanol or isopropanol; ethers, such as tetrahydrofuran or dioxane; benzene; formamides, such as dimethylformamide; and halogenated hydrocarbons.

The reaction according to prcess variant (a) is carried out in the presence of an acid-binding agent. All inorganic or organic acid-binding agents which can usually be employed can be added, such as alkali metal carbonates, for example sodium carbonate, potassium carbonate and sodium bicarbonate, or such as lower tertiary alkylamines, cycloalkylamines or aralkylamines, for example triethylamine and dimethylbenzylcyclohexylamine, or such as pyridine and diazobicyclooctane.

In process variant (a), the reaction temperatures can be varied within a substantial range. In general, the reaction is carried out at 20° to 150° C., preferably at 60° to 120° C. If a solvent is present, the reaction is suitably carried out at the boiling point of the particular solvent.

In carrying out process variant (a), it is preferred to use 2 moles of triazole and 1 mole of acid-binding agent per mole of the compound of the formula (II). It is possible to deviate from these amounts by up to about 20% in either direction.

To isolate the compound of the invention, the solvent may be distilled off, the residue taken up in an organic solvent and the solution washed with water. The organic phase may be dried over sodium sulfate and freed from the solvent in vacuo. The residue may be purified by distillation or recrystallization.

Preferred diluents which can be used for the reaction of process variant (b) include polar organic solvents. Preferred ones include nitriles, such as acetonitrile; sulfoxides, such as dimethylsulfoxide; formamides, such as dimethylformamide; ketones, such as acetone; ethers, such as diethyl ether and tetrahydrofuran; and chlorohydrocarbons, such as methylene chloride and chloroform.

In process variant (b), the reaction temperature can be varied within a substantial range. In general, the reaction is carried out at 0° to 100° C., preferably at 20° to 80° C. If a solvent is present, the reaction is suitably carried out at the boiling point of the particular solvent.

In carrying out process variant (b), it is preferred to use about 1 mole of sulfonyl-bis-1,2,4-triazole-(1) per mole of the compound of the formula (III). The sulfonylbis-1,2,4-triazol-(1) may be produced in situ.

To isolate the compounds of the formula (1), the solvent may be distilled off, the residue taken up in an organic solvent and the solution washed with water.

The organic phase may be dried over medium sulfate and freed from the solvent in vacuo. The residue may be purified by recrystallization or by forming a salt.

Diluents which can be used for the reaction of process variant (c/1) include polar organic solvents. Preferred ones include alcohols, such as methanol and ethanol, and nitriles, such as acetonitrile. The reaction is carried out in the presence of a reduction catalyst. Preferably, noble metal catalysts, noble metal oxide or noble metal hydroxide catalysts or so-called "Raney catalysts" are used, especially platinum, platinum oxide and nickel. The reaction temperatures can be varied within a substantial range. In general, the reaction is carried out at 20° to 50° C., preferably at 20° to 40° C. The reaction can be carried out under normal pressure, or under elevated pressure, for example, 1 to 2 atmospheres gauge. If the reaction follows variant (a), about 1 mole of hydrogen and 0.1 mole of catalyst may be employed per mole of the compound of the formula (II).

To isolate the compounds, the catalyst may be filtered off and freed from the solvent in vacuo and the resulting products of the formula (I) purified by distillation or recrystallization.

Where desired, the compounds according to the invention can be obtained in the form of salts by conversion in accordance with customary methods.

If variant (c/2) is followed, preferred diluents for the reaction are alcohols, such as isopropanol, or inert hydrocarbons, such as benzene. The reaction temperatures can again be varied within a substantial range; in general, the reaction is carried out at 20° to 120° C., preferably at 50° to 100° C. To carry out the reaction, about 1 to 2 moles of aluminum isopropylate are employed per mole of the starting compound. To isolate the compound of the formula (I), excess solvent may be removed by distillation in vacuo and the resulting aluminum compound decomposed with dilute sulfuric acid or sodium hydroxide solution. Further working up may be carried out in the usual manner.

If variant (c/3) is followed, polar organic solvents can be used as diluents for the reaction. Preferred ones include alcohols, such as methanol, ethanol, butanol or isopropanol, and ethers, such as diethyl ether or tetrahydrofuran. The reaction is generally carried out at 0° to 30° C. preferably at 0° to 20° C. For this reaction, about 1 mole of a complex hydride, such as sodium borohydride or lithium alanate, is generally employed per mole of the starting compound. To isolate the compounds of the formula (I), the residue may be taken up in dilute hydrochloric acid and the mixture then rendered alkaline and extracted with an organic solvent. Further working up may be carried out in the usual manner.

Diluents which can be used for the reaction according to the invention in accordance with process variant (c/4) include polar organic solvents, preferably alcohols, such as methanol and ethanol, and also water. The reaction temperatures can here again be varied within a substantial range; the reaction is generally carried out at temperatures of 20° to 100° C., preferably at 50° to 100° C. To carry out the reaction, about 1 to 3 moles of formamidine-sulfinic acid and 2 to 3 moles of alkali metal hydroxide may be employed per mole of the starting compound. To isolate the end products, the reaction mixture may be freed from the solvent and the residue extracted with water and organic solvents, worked up in the usual manner and purified; the salt may be prepared if desired.

ω-[1,2,4-Triazolyl-(1)]-2,4-dichloroacetophenone and the corresponding nitrate may be mentioned as particularly active compounds.

The active compounds according to the invention exhibit a strong fungitoxic action. They do not damage crop plants in the concentrations required to combat fungi. For these reasons, they can be used as plant protection agents for combating fungi. Fungitoxic agents are employed in plant protection to combat Archimycetes, Phycomycetes, Ascomycetes, Basidiomycetes and *Fungi Imperfecti*.

The active compounds according to the invention have a broad spectrum of action and can be used against parasitic fungi which infect the above-ground parts of plants or attack the plants through the soil, and also against seed-borne pathogens. They display a particularly good activity against parasitic fungi on aboveground parts of plants, such as species of Erysiphe, species of Podosphaera and species of Venturia, for example against the pathogen of powdery mildew of apples (*Podosphaera leucotricha*), of apple scab (*Fusicladium dendriticum*) and of powdery mildew of cucumbers (*Erysiphe cichoracearum*). Furthermore, they display a high level of activity against cereal diseases.

It is to be emphasised that the active compounds according to the invention not only display a protective action but can also be used systemically. Thus it proves possible to protect plants against fungal infection by supplying the active compound to the above-ground parts of the plants via the soil, via the plant or via the seed. As plant protection agents, the active compounds according to the invention can be used for the treatment of seed and for the treatment of above-ground parts of plants.

The compounds according to the invention are well tolerated by plants. They only have a low toxicity to warm-blooded animals and, because of their low odor and their good toleration by human skin, they are not unpleasant to handle.

The active compounds according to the instant invention can be utilized, if desired, in the form of the usual formulations or compositions with conventional inert (i.e. plant compatible or herbicidally inert) pesticide diluents or extenders, i.e., diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as ligain, sulfite waste liquors, methyl collulose, etc.

Such active compounds may be employed alone or in the form of mixtures with one another and/or with such solid and/or liquid dispersible carrier vehicles and/or with other known compatible active agents, especially plant protection agents, such as other fungicides, microbicides and plant growth regulants, or insecticides, acaricides, rodenticides, herbicides, fertilizers, bird repellents, agents for improving soil structure, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight of the mixture, whereas carrier composition mixtures suitable for direct application or field application generally contemplate those in which the active compound is present in an amount substantially between about 0.0001–10%, preferably 0.01–1%, by weight of the mixture. Thus, the present invention contemplates over-all compositions which comprise mixtures of a conventional dispersible carrier vehicle such as (1) a dispersible inert finely divided carrier solid, and/or (2) a dispersible carrier liquid such as an inert organic solvent and/or water preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

When the compounds are used as leaf fungicides, the concentrations of the active compound in the compositions for actual application can be varied within a substantial range. They are generally about 0.1 to 0.00001 percent by weight, preferably 0.05 to 0.0001%.

In the treatment of seed, amounts of active compound of 0.001 to 50 g per kilogram of seed, preferably 0.01 to 10 g, are generally applied to the seed.

For the treatment of soil, amounts of active compound of 1 to 1,000 g per cubic meter of soil, preferably 10 to 200 g, are generally applied to the soil.

The active compounds also exhibit a microbicidal activity. At relatively higher concentrations, they also have growth-regulating properties.

Furthermore, the present invention contemplates methods of selectively killing, combating or controlling fungi, microbes and plant growth, and more particularly methods of combating fungi, which comprises applying to at least one of correspondingly (a) such fungi, (b) such microbes, (c) such plants and (d) the corresponding habitat thereof, i.e. the locus to be protected, e.g. to a growing crop, to an area where a crop is to be grown or to a domestic animal, a correspondingly combative or toxic amount, i.e. a fungicidally, microbicidally or plant-growth regulating effective amount of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, dry dressing, moist dressing, wet dressing, slurry dressing, encrusting, and the like.

It will be realized of course that the concentration of the particular compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE 1

Erysiphe test/systemic
  Solvent: 4.7 parts by weight of acetone
  Dispersing agent: 0.3 part by weight of alkylaryl polyglycol ether
  Water: 95 parts by weight The amount of active compound required to give the desired concentration of active compound in the watering liquid was mixed with the stated amount of solvent and the concentrate was diluted with the stated amount of water which contained the stated additives.

Cucumber plants grown in standard soil, in the 1-2 leaf stage, were watered three times within one week with 10 cc of the watering liquid, of the stated concentration of active compound, per 100 cc of soil.

The plants treated in this way were inoculated, after treatment, with conidia of the fungus *Erysiphe cichoracearum*. The plants were then set up in a greenhouse at 23°-24° C. and 70% relative atmospheric humidity. After 12 days, the infection of the cucumber plants was determined as a percentage of the untreated, but also inoculated, control plants.

0% denotes no infection and 100% denotes that the infection was exactly as great as in the case of the control plants.

The active compounds, active compound concentrations and results can be seen from the table which follows:

TABLE 1

Erysiphe test/systemic

| Active compound | Infection in % of the infection of the untreated control at an active compound concentration of 25 ppm |
|---|---|
| 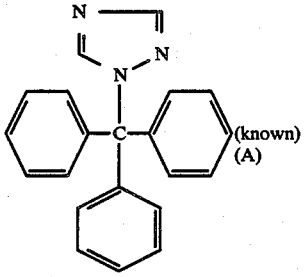 (known) (A) | 87 |
| 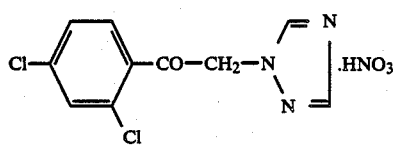 (15) | 1 |
| 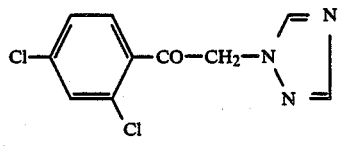 (3) | 1 |

TABLE 1-continued

Erysiphe test/systemic

| Active compound | Infection in % of the infection of the untreated control at an active compound concentration of 25 ppm |
|---|---|
| 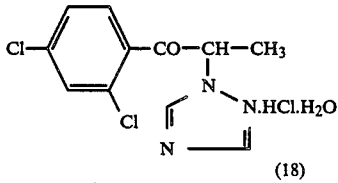 (18) | 0 |

EXAMPLE 2

Podophaera test/systemic
    Solvent: 4.7 parts by weight of acetone
    Dispersing agent: 0.3 part by weight of alkylaryl polyglycol ether
    Water: 95 parts by weight The amount of active compound required for the desired concentration of the active compound in the watering liquid was mixed with the stated amount of solvent and the concentrate was diluted with the stated amount of water which contained the stated additions.

Apple seedlings grown in standard soil, in the 3–4 leaf stage, were watered once within a week with 20 cc of the watering liquid, having the stated concentration of active compound, per 100 cc of soil.

After the treatment, the plants treated in this way were inoculated with conidia of *Podosphaera leucotricha* and placed in a greenhouse at a temperature of 21°–23° C. and a relative atmospheric humidity of approximately 70%. 10 days after the inoculation, the infection of the seedlings was determined as a percentage of the untreated but also inoculated control plants.

0% means no infection and 100% means that the infection was exactly as great as in the case of the control plants.

The active compounds, the concentrations of the active compounds and the results can be seen from the table which follows:

TABLE 2

Podosphaera test/systemic

| Active compound | Infection in % of the infection of the untreated control as an active compound concentration of 25 ppm |
|---|---|
| 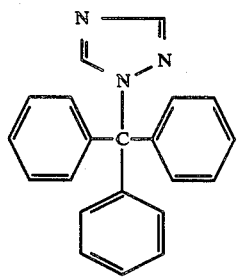 (known) (A) | 100 |

TABLE 2-continued

Podosphaera test/systemic

| Active compound | Infection in % of the infection of the untreated control as an active compound concentration of 25 ppm |
|---|---|
| 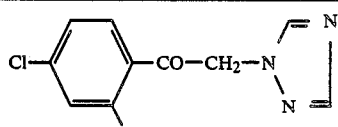 (3) | 1 |
| 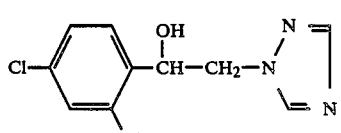 (28) | 1 |

EXAMPLE 3

Podosphaera test (powdery mildew of apples)/protective
    Solvent: 4.7 parts by weight of acetone
    Emulsifier: 0.3 part by weight of alkyl polyglycol ether
    Water: 95 parts by weight The amount of active compound required for the desired concentration of the active compound in the spray liquid was mixed with the stated amount of solvent, and the concentrate was diluted with the stated amount of water which contained the stated additions.

Young apple seedlings in the 4–6 leaf stage were sprayed with the spray liquid until dripping wet. The plants remained in a greenhouse for 24 hours at 20° C. and at a relative atmospheric humidity of 70%. They were then inoculated by dusting with conidia of the apple powdery mildew causative organism (*Podosphaera leucotricha*) and placed in a greenhouse at a temperature of 21°–23° C. and at a relative atmospheric humidity of about 70%.

Ten days after the inoculation, the infection of the seedlings was determined as a percentage of the untreated but also inoculated control plants.

0% means no infection: 100% means that the infection was exactly as great as in the case of the control plants.

The active compounds, the concentrations of the active compounds and the results can be seen from the following Table:

TABLE 3

Podosphaera test/protective

| Active compound | Infection in % of the infection of the untreated control at an active compound concentration of 0.00125% by weight |
|---|---|
| Triphenyl-triazolylmethane (known) (A) | 85 |
| 2,4-Cl,Cl-C₆H₃-CO-CH₂-N(triazole)·HNO₃ (15) | 39 |
| 2,4-Cl,Cl-C₆H₃-CO-CH₂-N(triazole) (3) | 39 |
| 2,4-Cl,Cl-C₆H₃-CH(OH)-CH₂-N(triazole) (28) | 31 |

EXAMPLE 4

Erysiphe test/protective
  Solvent: 4.7 parts by weight of acetone
  Emulsifier: 0.3 part by weight of alkyl polyglycol ether
  Water: 95 parts by weight The amount of the active compound required for the desired concentration of active compound in the spray liquid was mixed with the stated amount of the solvent, and the concentrate was diluted with the stated amount of water containing the stated additions.

Young cucumber plants with about three foliage leaves were sprayed with the spray liquid until dripping wet. The cucumber plants remained in a greenhouse for 24 hours to dry. They were then, for the purpose of inoculation, dusted with conidia of the fungus *Erysiphe cichoracearum*. The plants were subsequently placed in a greenhouse at 23°–24° C. and at a relative atmospheric humidity of about 75%.

After 12 days, the infection of the cucumber plants was determined as a percentage of the untreated but also inoculated control plants. 0% means no infection: 100% means that the infection was exactly as great as in the case of the control plants.

The active compounds, the concentrations of the active compounds and the results can be seen from the following Table:

TABLE 6

Erysiphe test/protective

| Active compound | Infection in % of the infection of the untreated control at an active compound concentration of 0.00062% by weight | 0.0005% |
|---|---|---|
| Triphenyl-triazolylmethane (known) (A) | 63 | |

TABLE 6-continued

Erysiphe test/protective

| Active compound | Infection in % of the infection of the untreated control at an active compound concentration of 0.00062% by weight | 0.0005% |
|---|---|---|
| Compound (3): 2,4-dichloro-phenyl-CO-CH$_2$-N(triazole) | 46 | — |
| Compound (28): 2,4-dichloro-phenyl-CH(OH)-CH$_2$-N(triazole) | — | 50 |
| Compound: 2,4-dichloro-phenyl-CO-CH(CH$_3$)-N(triazole)·HCl·H$_2$O | 21 | — |

EXAMPLE 5

Fusicladium test (apple scab)/protective
  Solvent: 4.7 parts by weight of acetone
  Emulsifier: 0.3 part by weight of alkylaryl polyglycol ether
  Water: 95 parts by weight The amount of active compound required for the desired concentration of the active compound in the spray liquid was mixed with the stated amount of solvent, and the concentrate was diluted with the stated amount of water which contained the stated additions.

Young apple seedlings in the 4–6 leaf stage were sprayed with the spray liquid until dripping wet. The plants remained in a greenhouse for 24 hours at 20° C. and at a relative atmospheric humidity of 70%. They were then inoculated with an aqueous conidium suspension of the apple scab causative organism (*Fusicladium dendriticum*) and incubated for 18 hours in a humidity chamber at 18°–20° C. and at a relative atmospheric humidity of 100%.

The plants then again came into a greenhouse for 14 days.

15 days after inoculation, the infection of the seedlings was determined as a percentage of the untreated but also inoculated control plants.

0% means no infection; 100% means that the infection was exactly as great as in the case of the control plants.

The active compound, the concentrations of the active compounds and the results can be seen from the following table:

TABLE 5

Fusicladium test/protective

| Active compound | Infection in % of the infection of the untreated control at an active compound concentration of 0.0025% by weight |
|---|---|
| (A) (known): triphenylmethyl-triazole | 76 |
| (3): 2,4-dichloro-phenyl-CO-CH$_2$-N(triazole) | 22 |
| (28): 2,4-dichloro-phenyl-CH(OH)-CH$_2$-N(triazole) | 57 |
| (16): 4-chloro-phenyl-CO-CH(CH$_3$)-N(triazole) | 71 |

TABLE 5-continued

Fusicladium test/protective

| Active compound | Infection in % of the infection of the untreated control at an active compound concentration of 0.0025% by weight |
|---|---|
| 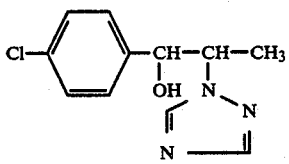 (29) | 67 |

The following further examples are set forth to illustrate, without limitation, the manner of producing the instant compounds according to the present invention:

Process variant (a):

EXAMPLE 6

(a) 196 g (1 mole) of phenyl benzyl ketone were suspended in 1 liter of carbon tetrachloride. A solution of 51 ml (1 mole) of bromine in 50 ml of carbon tetrachloride were added dropwise, under irradiation (UV), at a rate such that a steady consumption of bromine took place. The solvent was then distilled off in a water pump vacuum. 274 g (quantitative yield) of ω-bromo-ω-phenyl-acetophenone of melting point 48°–50° C. were obtained.

(b)

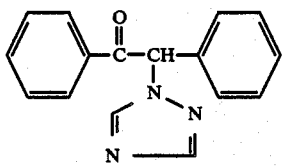 (1)

138 g (0.5 mole) of ω-bromo-ω-phenyl-acetophenone (desyl bromide) were dissolved in 200 ml of dimethylformamide. This solution was added dropwise at room temperature, while cooling with water, to a mixture of 69 g (1 mole) of 1,2,4-triasole and 51 g (0.5 mole) of triethylamine in 200 ml of dimethylformamide. The reaction mixture was stirred for a further 15 hours at room temperature, then poured into 2.5 liters of water and extracted twice with 500 ml of chloroform. The chloroform solution was washed repeatedly with water and dried over sodium sulfate. The solvent was then distilled off in a water pump vacuum. The solid residue was boiled up in 500 ml of ligroin. After adding 500 ml of ethyl acetate, the mixture was heated under reflux for about one hour and was then filtered hot. The desired end product crystallized out from the cooling filtrate in the form of colorless crystals. 83 g (65% of theory) of ω-[1,2,4-triasolyl-(1)]-ω-phenyl-acetophenone of melting point 110°–117° C. were obtained.

EXAMPLE 7

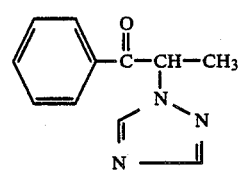 (2)

42.6 g (0.2 mole) of ω-bromo-propiophenone were dissolved in 50 ml of acetone. This solution was added dropwise to a suspension, boiling under reflux, of 21 g (0.3 mole) of 1,2,4-triasole and 60 g of potassium carbonate in 200 ml of acetone. After heating under reflux for 15 hours, the suspension was filtered when cold, the filtrate was freed from the solvent in a water pump vacuum, the residue was taken up in 200 ml of methylene chloride and the solution was washed twice with 100 ml of water, dried over sodium sulfate and freed from the solvent in a water pump vacuum. The residue was dissolved in 50 ml of ethyl acetate and diisopropyl ether was added, at the boil, until the mixture turned cloudy. It was allowed to cool and the colorless crystals which had precipitated were filtered off. 32.2 g (80% of theory) of -[1,2,4-triasolyl-(1)][-propiophenone of melting point 89°–91° C. were obtained.

EXAMPLE 8

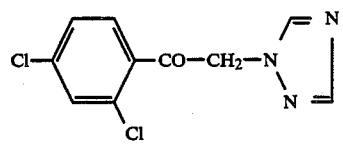 (3)

269 g (1 mole) of ω-bromo-2,4-dichloroacetophenone were dissolved in 250 ml of acetonitrile. This solution was added dropwise to a suspension, boiling under reflux, of 69 g of 1,2,4-triasole (1 mole) and 150 g of potassium carbonate in 2 liters of acetonitrile. After heating for 18 to 24 hours under reflux, the suspension was filtered when cold, the filtrate was freed from the solvent, the residue was taken up in ethyl acetate, and the solution was washed with water, dried over sodium sulfate and freed from the solvent. On adding isopropanol, the residue from evaporation of the ethyl acetate crystallized out. After recrystallization from ligroin-/isopropanol, 154 g (60% of theory) of ω-[1,2,4-triasolyl-(1)]-2,4-dichloroacetophenone of melting point 117° C. were obtained.

EXAMPLE 9

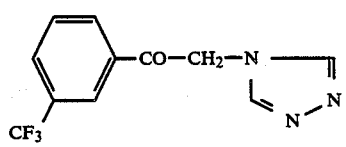 (4)

14 g (0.2 mole) of 1,2,4-triasole and 10.2 g (0.1 mole) of triethylamine were dissolved in 250 ml of dimethylformamide. 26.7 g (0.1 mole) of ω-bromo-3-trifluoromethylacetophenone, dissolved in 50 ml of dimethylformamide were added dropwise, while stirring, to the above mixture, which was well cooled with ice water.

The reaction mixture was then stirred for several hours longer at room temperature and poured into 750 ml of water, and the whole was then extracted by shaking with methylene chloride. The organic phase was isolated. The oil which remained after distilling off the solvent was taken up in ethyl acetate. This solution was saturated with hydrogen chloride gas. The salt mixture which remained after distilling off the solvent, and which did not crystallize, was digested with 200 ml of water. The water-insoluble portion contained the 1,2,4-triasole-(1) isomer. The water-soluble portion, which contained the 1,2,4-triasolyl-(4) isomer, was rendered alkaline with sodium carbonate solution and the oil which precipitated was taken up in ether. The ether residue crystallized on trituration with ligroin. After recrystallization from ligroin/isopropanol, 5 g (15% of theory) of ω-[1,2,4-triasolyl-(4)]-3-trifluoromethylacetophenone of melting point 152° C. were obtained.

Further, the following compounds of the general formula

TABLE 6

$$R^1-\overset{O}{\underset{}{C}}-\overset{}{\underset{\substack{N\\ \parallel\\ N}}{C}H}-R^2$$

were obtained:

| Compound No. | $R^1$ | $R^2$ | Melting point °C. |
|---|---|---|---|
| 5 | biphenyl | H | 176 |
| 6 | Cl-biphenyl | H | 213 |
| 7 | Cl-phenyl | H | 153 |
| 8 | CH₃-phenyl | H | 112 |
| 9 | F-phenyl | H | 130 |
| 10 | 3-CF₃-phenyl | H | 72 |
| 11 | CH₃O-phenyl | H | 242 (HCl-Salt) |
| 12 | 3-Cl-phenyl | H | 106 |
| 13 | 3,4-Cl₂-phenyl | H | 170 |
| 14 | phenyl | H | 119 |

TABLE 6-continued $$R^1-\overset{O}{\underset{}{C}}-\overset{}{\underset{\substack{N\\ \parallel\\ N}}{C}H}-R^2$$

were obtained:

| Compound No. | $R^1$ | $R^2$ | Melting point °C. |
|---|---|---|---|
| 15 | 3,4-Cl₂-phenyl | H | 138 (HNO₃-Salt) |
| 16 | Cl-phenyl | CH₃ | 76–78 |
| 17 | 3,4-Cl₂-phenyl | CH₃ | 166–170 (HCl-Salt) |
| 18 | 3,4-Cl₂-phenyl | CH₃ | 153–155 (HCl × H₂O) |
| 19 | (CH₃)₃C— | phenyl | 155–157 |
| 20 | (CH₃)₃C— | H | BP 90–95° C./ 0.02 mm |
| 21 | CH₃ | phenyl | 133–138 (HCl-Salt) |
| 22 | phenyl | 4-Cl-phenyl | 112–122 |
| 23 | Cl-phenyl | phenyl | 133–134 |
| 24 | Cl-phenyl | Cl-phenyl | 172–180 |
| 25 | F-phenyl | Cl-phenyl | 176–177 |
| 26 | CH₂—CH₂—CH₂—CH₂ | | 150 (HCl-Salt) |
| 26a | phenyl-O-phenyl | H | 130 (HNO₃-Salt) (decomposition) |

Process variant (b):

EXAMPLE 10

(a) 93 g (4 moles) of sodium were suspended in 300 ml of toluene. 830 ml of toluene were added and 260 g (2 moles) of pivalic acid ethyl ester were then added dropwise at 50° to 60° C. over the course of 3.5 hours, while stirring. The mixture was stirred overnight at room temperature. 210 g of concentrated sulfuric acid in 350 ml of water were then added dropwise over the course of 2 hours at 15° C. The precipitate which had separated out was filtered off and washed twice with 100 ml of water. The organic phase was isolated and then distilled in vacuo. The fraction obtained at 60°-80° C./15 mm was recrystallized from petroleum ether. 84.3 g (49% of theory) of di-tert.-butylacyloin of melting point 78°-80° C. were obtained.

(b)

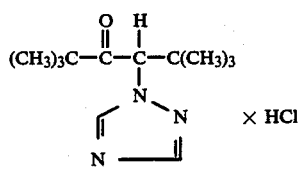
(27)

17.2 g (0.1 mole) of di-tert.-butylacyloin were dissolved in 100 ml of absolute acetonitrile. 49 g (0.7 mole) of 1,2,4-triasole were added, and 11 ml (0.15 mole) of thionyl chloride were then added dropwise with slight cooling. After the dropwise addition, the mixture was stirred for 48 hours at 50° C., the solvent was then distilled off in vacuo, the residue was taken up in 100 ml of methylene chloride and the solution was washed twice with 100 ml of water. The organic phase was dried over sodium sulfate and filtered, and the solvent was distilled off in vacuo. The oil which remained was taken up in 300 ml of ethyl acetate, the solution was filtered and a solution of hydrochloric acid in ether was added. The precipitate was filtered off and recrystallized from acetone. 1.7 g (6.6% of theory) of the hydrochloride of 2,2-5,5-tetramethyl-3-[1,2,4-triasolyl-(1)]-hexan-4-one of melting point 148°-152 C., with decomposition, were obtained.

Process variant (c)

EXAMPLE 11

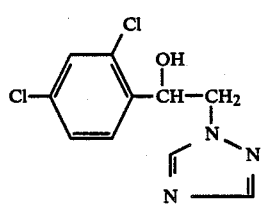
(28)

25.6 g (0.1 mole) of ω-[1,2,4-triasolyl-(1)]-2,4-dichloroacetophenone were dissolved in 610 ml of methanol and 6.3 g (0.15 mole) of sodium borohydride were added in portions at 5° to 10° C., while stirring. The mixture was then stirred for one hour at room temperature and heated to the boil for one hour. After distilling off the solvent, 250 ml of water and 50 ml of concentrated hydrochloric acid were added to the residue and the mixture was boiled up for 15 minutes. After rendering the reaction mixture alkaline with sodium hydroxide solution, the solid reaction product was filtered off. It was recrystallized from aqueous acetonitrile. 12 g (42% of theory) of 1-[1,2,4-triasolyl-(1)]-2-(2,4-dichlorophenyl)-ethan-2-ol of melting point 87° C. were obtained.

The following compounds of the general formula

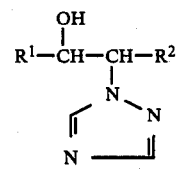
(V)

were obtained analogously:

TABLE 7

| Compound No. | R¹ | R² | Melting Point °C. |
|---|---|---|---|
| 29 | Cl—⟨phenyl⟩— | CH₃ | 113–116 |
| 30 | ⟨phenyl⟩— | —⟨phenyl⟩—Cl | 123–128 |
| 31 | Cl—⟨phenyl⟩— | —⟨phenyl⟩ | 144–152 |
| 32 | Cl—⟨phenyl⟩— | —⟨phenyl⟩—Cl | 192–195 |
| 33 | ⟨phenyl-phenyl⟩— | H | 182 |
| 34 | Cl—⟨phenyl-phenyl⟩— | H | 220 |
| 34a | ⟨phenyl⟩—O—⟨phenyl⟩ | H | |

Other compounds which can be similarly prepared include:

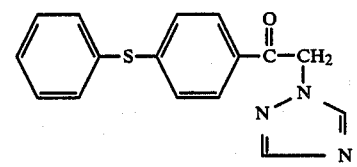

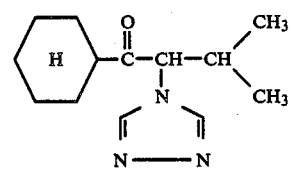

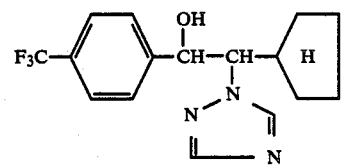

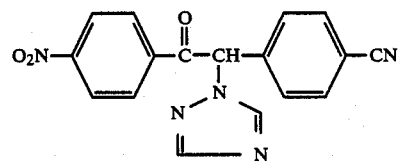

-continued

[Chemical structures shown]

It will be appreciated that the instant specification and claims are set forth by way of illustration and not limitation, and that various modifications and changes may be made without departing from the spirit and scope of the present invention.

What is claimed is:

1. A triazolyl-alkanone of the formula $$R^1-CO-CH-R^2$$

[with triazolyl substituent on CH]

in which
$R^1$ is alkyl with up to 6 carbon atoms; and
$R^2$ is hydrogen; alkyl with up to 6 carbon atoms; cycloalkyl with 3 to 8 carbon atoms; phenyl; or phenyl substituted by alkyl or alkoxy each with up to 4 carbon atoms, haloalkyl with up to 4 carbon atoms and up to 5 halogen atoms, halogen, cyano, nitro, dialkylamino with up to 4 carbon atoms in each alkyl moiety, alkoxy-carbonyl with 2 to 4 carbon atoms, alkyl-sulfonyl or haloalkylsulfonyl each with up to 4 carbon atoms and in the latter case with up to 5 halogen atoms, phenylsulfonyl, phenyl or chlorophenyl,
or a salt thereof.

2. A compound according to claim 1 in which $R^2$ is hydrogen or methyl.

3. A compound according to claim 1 wherein such compound is 4-[1,2,4-triazolyl-(1)]-2,2-dimethyl-butanone-3- of the formula $$(CH_3)_3C-CO-CH_2-N\begin{array}{c}N\\\|\\N\end{array}$$

4. A fungicidal composition of matter comprising a fungicidally effective amount of a compound or salt according to claim 1.

5. A method of combating fungi comprising applying to such fungi or to a habitat thereof a fungicidally effective amount of a compound or salt according to claim 1.

6. A method according the claim 5, wherein such compound is 4-[1,2,4-triazolyl-(1)]-2,2-dimethyl-butanone-3.

7. A compound of the formula $$N-N-\overset{H}{\underset{R_4}{C}}-Z-R_5$$

wherein
$R_4$ is hydrogen, $C_{1-6}$-alkyl or phenyl,
$R_5$ is $C_{1-6}$-alkyl or cycloalkyl, and
Z is C=O,
or a fungicidal salt of said compound.

8. A method of combating fungi comprising applying to such fungi or to a habitat thereof a fungicidally effective amount of a compound or salt according to claim 7.

* * * * *

UNITED STATES PATENT AND TRADEMARK OFFICE
CERTIFICATE OF CORRECTION

PATENT NO. : 4,776,877
DATED : October 11, 1988
INVENTOR(S) : Helmut Timmler, et al It is certified that error appears in the above-identified patent and that said Letters Patent is hereby corrected as shown below:

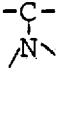

Col. 3, line 28 — Beginning of formula delete "(CH₃)₂C-" and substitute --(CH₃)₃C- --

Col. 3, line 34 — Middle of formula delete "N" and substitute --H--

Col. 3, line 48 and Col. 3, line 55 — Middle of formula delete "-CH₃- and substitute -- -CH₂- --

Col. 5, line 7 — Delete "prcess" and substitute --process--

Col. 5, line 48 — Delete "nylbis" and substitute --nyl-bis--

Col. 5, line 52 — Delete "medium" and substitute --sodium--

Col. 8, line 7 — Delete "ligain" and substitute --lignin--

Col. 8, line 8 — Correct --cellulose--

Col. 11, line 21 — Correct --Podosphaera--

Col. 14, line 53 and Col. 15, line 1 — Delete "TABLE 6" and substitute --TABLE 4--

Col. 17, line 67, Col. 18, lines 27, 50-51 Col. 19, lines 12, 17; Col. 21, lines 35, 51, 65 — Delete "triasolyl" and substitute --triazolyl--

Col. 18, lines 15, 41, 63; Col. 19, line 11 — Delete "triasole" and substitute --triazole--

UNITED STATES PATENT AND TRADEMARK OFFICE
CERTIFICATE OF CORRECTION

PATENT NO. : 4,776,877
DATED : October 11, 1988
INVENTOR(S) : Helmut Timmler, et al It is certified that error appears in the above-identified patent and that said Letters Patent is hereby corrected as shown below:

Col. 20, line 62        Delete "830 ml" and substitute --850 ml--

Signed and Sealed this

Fifth Day of September, 1989

Attest:

DONALD J. QUIGG

Attesting Officer

Commissioner of Patents and Trademarks